United States Patent [19]

Fretto

[11] Patent Number: 5,268,358
[45] Date of Patent: Dec. 7, 1993

[54] PDGF RECEPTOR BLOCKING PEPTIDES

[75] Inventor: Larry J. Fretto, Sausalito, Calif.

[73] Assignee: Cor Therapeutics, Inc., Palo Alto, Calif.

[21] Appl. No.: 701,350

[22] Filed: May 6, 1991

Related U.S. Application Data

[63] Continuation of Ser. No. 282,249, Dec. 8, 1988, abandoned.

[51] Int. Cl.$^5$ ............... C07K 7/06; C07K 7/08; C07K 7/10; A61K 37/02
[52] U.S. Cl. ............................. 514/12; 514/15; 514/17; 530/324; 530/325; 530/329; 530/350
[58] Field of Search ............ 530/324, 325, 329; 514/12, 17, 15

[56] References Cited

U.S. PATENT DOCUMENTS 4,845,075 7/1989 Murray et al. ............... 514/12

OTHER PUBLICATIONS

S. Devare, E. P. Reddy, J. D. Law, K. Robbins, and S. Aaronson (1983), "Nucleotide sequence of the simian sarcoma virus genome: Demonstration that its acquired cellular sequences encode the transforming gene product p.28$^{sis}$," *Proc. Natl. Acad. Sci. USA* 80:731–735.

H. Niman (1984), "Antisera to a synthetic peptide predicted by the nucleotide sequence of the sis viral oncogene recognize human platelet derived growth factor," *Hybridoma* 3(1):61 (Abstract).

H. Niman, R. Houghten, and D. Bowen-Pope (1984), "Detection of high molecular weight forms of platelet-derived growth factor by sequence-specific antisera," *Science* 226:701–703.

M. Waterfield, G. Scrace, N. Whittle, P. Stroobant, A. Johnsson, A. Wasteson, B. Westermark, C.-H. Heldin, J. Huang, and T. Deuel (1983), "Platelet-derived growth factor is structurally related to the putative transforming protein p. 28$^{sis}$ of simian sarcoma virus," *Nature* 304:35–39.

H. Niman (1984), "Antisera to a synthetic peptide of the sis viral oncogene product recognize human platelet-derived growth factor," *Nature* 307:180–183.

M. Hannink, M. Sauer, and D. Donoghue (1986), "Deletions in the C-terminal coding region of the v-sis gene: Dimerization is required for transformation," *Mol. Cell. Biol.* 6:1304–1314.

M. Sauer, M. Hannink, and D. Donoghue (1986), "Deletions in the N-terminal coding region of the v-sis gene: Determination of the minimal transforming region," *J. Virol.* 59:292–300.

D. Bonthron, C. Morton, S. Orkin, and T. Collins (1988), "Platelet-derived growth factor A chain: Gene structure, chromosomal location, and basis for alternative mRNA splicing," *Proc. Natl. Acad. Sci. USA* 85:1492–1496.

N. Giese, K. Robbins, and S. Aaronson (1987), "The role of individual cysteine residues in the structure and function of the v-sis gene product," *Science* 236:1315–1318.

M. Sauer and D. Donoghue (1988), "Identification of nonessential disulfide bonds and altered conformations in the v-sis protein, a homolog of the B chain of platelet-derived growth factor," *Mol. Cell. Biol.* 8:1011–1018.

(List continued on next page.)

Primary Examiner—Robert A. Wax
Assistant Examiner—Keith C. Furman
Attorney, Agent, or Firm—Townsend & Townsend Khourie and Crew

[57] ABSTRACT

Methods and compositions are provided for treating several acute disease states associated with smooth muscle cell proliferation as well as the chronic process of atherogenesis utilizing oligopeptides corresponding to regions of the PDGF receptor protein. The oligopeptides can be used to block PDGF binding and activation for numerous applications, and can serve as immunogens to raise receptor-specific antibodies.

5 Claims, No Drawings

OTHER PUBLICATIONS

R. Doolittle, M. Hunkapiller, L. Hood, S. Devare, K. Robbins, S. Aaronson, and H. Antoniades (19893), "Simian sarcoma virus onc gene, v-sis, is derived from the gene (or genes) encoding a platelet-derived growth factor," *Science* 221:275–277 (1983).

K. Robbins, H. Antoniades, S. Devare, M. Hunkapiller, and S. Aaronson (1983), "Structural and immunological similarities between simian sarcoma virus gene product(s) and human platelet-derived growth factor," *Nature* 305:605–608.

T. Deuel, J. Huang, S. Huang, P. Stroobant, and M. Waterfield (1983), "Expression of a platelet-derived growth factor-like protein in simian sarcoma virus transformed cells," *Science* 221:1348–1350 (1983).

H. Antoniades (1981), "Human platelet-derived growth factor (PDGF): Purification of PDGF-I and PDGF-II and separation of their reduced subunits," *Proc. Natl. Acad. Sci.* 78:7314–7317.

C. Betsholtz, A. Johnsson, C. H. Heldin, B. Westermark, P. Lind, M. Urdea, R. Eddy, T. Shows, K. Philpott, A. Mellor, T. Knott, and J. Scott, (1986) "cDNA sequence and chromosomal localization of human platelet-derived growth factor A-chain and its expression in tumor cell lines," *Nature* 320:695–699.

T. Daniel, P. Tremble, A. Frackelton, Jr., and L. Williams, (1985) "Purification of the PDGF receptor by using an anti-phosphotyrosine antibody," *Proc. Natl. Acad. Sci. USA* 82:2684–2687.

J. Escobedo, M. Keating, H. Ives, and L. Williams (1988), "Platelet-derived growth factor receptors expressed by cDNA transfection couple to a diverse group of cellular responses associated with cell proliferation," *J. Biol. Chem.* 263:1482–1487.

J. Escobedo, S. Navankasatussas, L. Cousens, S. Coughlin, G. Bell, and L. Williams (1988), "A common PDGF Receptor is Activated by Homodimeric A and B forms of PDGF," *Science* 240:1532–1534.

PDGF RECEPTOR BLOCKING PEPTIDES

This is a continuation of application Ser. No. 07/282,249, filed Dec. 8, 1988, now abandoned.

FIELD OF THE INVENTION

The present invention relates generally to novel therapeutic agents and, more particularly, to compositions and methods for the prevention and treatment of diseases involving undesirable proliferative effects of platelet-derived growth factor (PDGF) on smooth muscle cells.

BACKGROUND OF THE INVENTION

Cardiovascular disease is a major cause of human morbidity and mortality in modern societies. Atherogenesis, the process by which vascular narrowings are formed, often results following vascular injury and is caused by the migration and subsequent proliferation of smooth muscle cells from the arterial media into the arterial intima of the afflicted vessels. Smooth muscle cell migration and proliferation are key events in the restenosis that occurs after angioplasty, atheroectomy, endarterectomy, and other similar procedures.

A major stimulus for smooth muscle cell migration and proliferation following vascular injury is believed to be platelet-derived growth factor (PDGF). PDGF is released from activated platelets at the site of vascular injury, whether the injury is due to mechanical, immune-mediated, or metabolic causes. PDGF can also be produced locally by activated macrophages, endothelial and smooth muscle cells. PDGF is a potent chemotactic agent and mitogen for both vascular smooth muscle cells and fibroblasts. Smooth muscle cells within proliferative lesions express many more receptors for PDGF than those cells residing within the normal vessel wall, suggesting that the cells which migrate to and proliferate within the lesion are selected for responsiveness to PDGF. PDGF acts by binding to and activating a specific cell surface receptor. The activated receptor then transmits signals to the cell cytoplasm and/or nucleus, thereby effectuating migration and proliferation.

New therapeutic treatment regimens are urgently needed for preventing or reversing the chronic and debilitating process of atherogenesis and related cardiovascular diseases. Compositions which block the binding of PDGF to its cellular receptor molecule, thereby preventing PDGF-induced cell migration and proliferation, may provide major therapeutic benefits for treating or preventing atherogenesis and may be useful in other related acute disease states. Ideally, the new agents will be potent, relatively non-immunogenic to most patients, easy to administer, stable in vitro and resistant to degradation in vivo, and economical to produce. Further, these agents should be capable of functioning at the earliest stages of smooth muscle cell migration and proliferation without interfering with long-term wound healing. The present invention fulfills these and other related needs.

SUMMARY OF THE INVENTION

Novel methods and compositions are provided for inhibiting smooth muscle cell migration and proliferation and other activities utilizing oligopeptides capable of specifically binding to PDGF and/or its receptor and thereby blocking or inhibiting the activation of the PDGF receptor or the activation of cells expressing the PDGF receptor molecule. The oligopeptides will typically comprise at least about five to twenty amino acids and are thus relatively non-immunogenic and easy to produce, formulate and administer. These oligopeptides will be useful in treating a variety of diseases related to proliferation of smooth muscle cells including, but not limited to, atherogenesis.

DESCRIPTION OF THE SPECIFIC EMBODIMENTS

The present invention provides novel compositions and methods for treating PDGF-related proliferative syndromes by preventing or substantially inhibiting PDGF-induced cell growth in mesenchymal tissues. More specifically, oligopeptides mimicking regions of the PDGF receptor molecule are utilized to prevent the proliferative potential of the PDGF ligand by blocking its interaction with its cellular receptor. In this regard, the term "blocking oligopeptide" indicates a peptide capable of binding to PDGF and/or its receptor and interfering with the cellular activation process normally induced by PDGF. The peptides have a variety of other utilities, including use as an immunogen to raise antibodies against the receptor.

The blocking oligopeptides can be used individually or in combination for the treatment regimens. Depending upon the particular use, the peptides may be labeled or unlabeled, conjugated to carriers, admixed with other compounds, or the like.

Typically, the peptides of interest will be, derived from the extracellular amino-terminal portion of the PDGF receptor, which encodes the ligand binding domain for PDGF (Williams, et al., *Cold Spring Harbor Symposium*, (1988) 53:455-465, which is incorporated herein by reference). This extracellular portion of the receptor comprises five immunoglobulin-like domains (constant or variable). Comparison of the receptor domains with the well known structure of the immunoglobulin domains allows the identification in the receptor of amino acid sequences analogous to immunoglobulin complementarity determining regions (CDRs), which form the contact sites between the antigen and the antibody. Preferably, the peptides will comprise contiguous stretches spanning the putative CDRs of the receptor as shown in Table 1. Table 2 presents several peptides (I-XI) from this region. Other peptides of the present invention are prepared from regions of the receptor that show the highest degree of conservation between human and mouse extracellular domain of the receptor. Example sequences of this type are also listed in Table 2 (XII-XVII).

Preferably, peptides acting as "blocking oligopeptides" will comprise contiguous stretches within the sequences shown in Table 1. Of the seventeen preferred peptides of the present invention listed in Table 2, each may include additional (generally less than about 50) natively-associated amino acids (i.e., from the naturally-occurring PDGF receptor sequence) or other additional components.

TABLE 1

AMINO ACID RESIDUES OF THE LIGAND-BINDING DOMAINS FOR PDGF*

Domain 1

(1)                                                                                                                  (91)
LVVTPPGPELVLNVSSTFVLT C SGSAP.....VVWERMSQEP............PQEMAKAQDGTFSSVLTLTNLTGLDTGEYF C THNDSRGLETDERKRLYIFVPDP

Domain 2

(92)                                                                                   (181)
TVGFLPNDAEELFIFLTETEITIP C RVTD..PQLVVTLHEKKGDV.............ALPVPYDHQRGFS...GIFEDRSYI C KTTIGDREVDSDAYYVYRLQVSS

Domain 3

(182)                                                                                   (282)
INVSVNAVQT.VVR.QGENITLM C IVIGNE.VVNFEWTYPRKESGRLVEP............VTDFLLDMPYHIRSILHIPSAELEDSGTYT C NVTESVNDHQDEKAINITVVESG

Domain 4

(283)                                                                                   (384)
YVRLLGEVGTLQFAELHRSRTLQ V VFEAYPP.PTVLWFKDNRTLGDSSAG..........EIALSTRNVSETRYVSEITLVRVKVAEARHYT M RAFHEDAEVQLSFQLQINVP

Domain 5

(385)                                                                                   (499)
VRVLELSESHPDSGEQTVR C RGRGMPQ.PNIIWSACRD.LKRCPRELPPTLLGNSSEEESQLETNVTYWEEEQEFEVVSTLRLQHVDRPLSVR C TLRNAVGQDTQEVIVVP......HSLPFH

Abbreviations for Amino Acids

| | | | |
|---|---|---|---|
| A—Alanine (Ala) | G—Glycine (Gly) | M—Methionine (Met) | S—Serine (Ser) |
| C—Cysteine (Cys) | H—Histidine (His) | N—Asparagine (Asn) | T—Threonine (Thr) |
| D—Aspartic Acid (Asp) | I—Isoleucine (Ile) | P—Proline (Pro) | V—Valine (Val) |
| E—Glutamatic Acid (Glu) | K—Lysine (Lys) | Q—Glutamine (Gln) | W—Tryptophan (Trp) |
| F—Phenylalanine (Phe) | L—Leucine (Leu) | R—Arginine (Arg) | Y—Tyrosine (Tyr) |

*Note:
The domain sequences have been aligned using dots as spacers.

TABLE 2

Peptides Acting as "Blocking Oligopeptides"

Peptide:

I. X[1]—V—L—T—C—S—G—S—A—P—V—V—W—E—R—M—S—Z[2]
II. X—G—E—Y—F—C—T—H—N—D—S—R—G—L—E—T—D—E—R—K—R—L—Z
III. X—T—I—P—C—R—V—T—D—P—Q—L—V—V—T—L—H—Z
IV. X—R—S—Y—I—C—K—T—T—I—G—D—R—E—V—D—S—D—A—Y—Y—V—Z
V. X—T—L—M—C—I—V—I—G—N—E—V—V—N—F—E—W—Z
VI. X—T—Y—T—C—N—V—T—E—S—V—N—D—H—Q—D—E—K—A—I—N—Z
VII. X—T—L—Q—V—V—F—E—A—Y—P—P—P—T—V—L—W—Z
VIII. X—H—Y—T—M—R—A—F—H—E—D—A—E—V—Q—L—S—F—Q—L—Q—Z
IX. X—T—V—R—C—R—G—R—G—M—P—Q—P—N—I—I—W—Z
X. X—K—R—C—P—R—E—L—P—P—T—L—L—G—N—S—S—E—E—E—S—Z
XI. X—S—V—R—C—T—L—R—N—A—V—G—Q—D—T—Q—E—V—I—V—V—Z
XII. X—Q—D—G—T—F—S—S—V—L—T—L—T—Z
XIII. X—L—Q—V—S—I—N—V—S—V—N—A—V—Q—T—V—V—R—Q—G—Z
XIV. X—S—G—R—L—V—E—P—V—T—D—Z
XV. X—S—I—L—H—I—P—S—A—E—L—Z
XVI. X—E—T—R—Y—V—S—E—I—T—L—V—R—V—K—V—Z
XVII. X—I—N—V—P—V—R—V—L—E—L—S—E—S—H—P—Z

[1]X, if present, is hydrogen, amido, acetyl, or additionally includes an amino acid, dipeptide, tripeptide or an oligopeptide of up to 50 amino acid residues, including amino-terminal acetyl derivatives thereof.
[2]Z, if present, is hydroxyl, amido, or additionally includes an amino acid, dipeptide, tripeptide or an oligopeptide of up to 50 amino acid residues, including carboxy-terminal amide derivatives thereof, with the proviso that when X is also present the total additional amino acid residues (X + Z) will generally not exceed about 50, and also provided that the modifications do not adversely effect all of the desired activities of the subject compounds.

The peptides of interest will include at least about 5 but generally less than about 50 amino acids, preferably 8 to 20, and usually fewer than about 35 amino acids. In each instance, the oligopeptide will be as small as possible, while still maintaining substantially all of the desired activity, e.g., blocking activity. Although it may be preferable in some instances to utilize homopolymers of active oligopeptides, in other instances it may also be desirable to join two or more oligopeptides from the same domains or from different regions, which separately or together provide the desired activities. The peptides may, of course, be fused, bonded, mixed with, linked to, or conjugated or complexed with other proteins or molecules with desired activities (e.g., thrombolytic activity), preferably those having the same or a complementary range of biologic activities to obtain the benefits of the present invention.

It will be readily appreciated by skilled artisans that the peptides employed in the subject invention need not be identical to any particular of the most preferred polypeptide sequences shown in Table 2, so long as the subject compound is able to provide blocking or other desired activities at a sufficient level. Therefore, the peptides may be subject to various changes, such as insertions, deletions, substitutions, either conservative or non-conservative, to provide for certain advantages in their use. Conservative substitutions are typically within groups. The amino acid residues are thus usually replaced with functionally equivalent residues; for example basic polar amino acids can be replaced with other basic polar amino acids and acidic polar amino acids can be replaced with other acid polar amino acids. Examples of such substitutions include, inter alia. Gly, Ala; Val, Ile, Leu; Asp, Glu; Asn, Gln; Ser, Thr; Lys, Arg; Phe, Tyr; and Nor (norleucine), Met. Usually, the final sequence will not differ by more than about 10–40% from the naturally-occurring sequence, except e.g., where additional amino acids may be added at either terminus for other utilities, including conjugation to carriers.

The peptide in which an amino acid sequence has been modified by the substitution, addition or deletion of amino acid residues should not destroy the blocking activity and preferably should retain substantially all of the blocking activity of the unmodified peptides, and may contain enhanced blocking activity when compared to the unmodified peptides.

A spectrum of magnitudes of biological activity may be realized from the variant and derivative oligopeptides of the present invention. The amino acid substitutions, deletions or additions which may be made in the oligopeptides may modify the three-dimensional structure of the oligopeptide of the native, authentic sequence without significantly affecting its biological activity; or, the three-dimensional structure may be modified resulting in an alteration of the biological activity without destroying it; or, the biological activity of the oligopeptide may be altered without significantly changing the three-dimensional structure. The activity of the various peptides may be conveniently measured by assay techniques disclosed herein including analogous "competitive displacement" receptor binding assays known in the art.

Further, mosaics of portions of the oligopeptides or their derivatives may also be used within the present invention. The term "mosaic," as used herein, includes contiguous portions of the oligopeptides sufficient to encode a molecule having blocking activity as defined herein. The constituent portions of the mosaic can be chosen from any of the oligopeptides, as well as variants or derivatives thereof.

Also, the D-isomer form of one or more of the amino acids may be used, as desired, to modify biological properties, such as activity, rate of breakdown, etc. Thus, while the amino acids of these compounds are normally in the natural L form, one or more, usually two or less and preferably one amino acid may be replaced with the optical isomer D form, or a D, L-racemic mixture can be provided in the molecules comprising the oligopeptide compound.

Other modifications to the peptides can include the addition of one, two or more amino acids to the termini, such as to provide facilitated linking capability or to further modify the oligopeptide's physical or chemical properties. Amino acids such as tyrosine, cysteine, lysine, glutamic or aspartic acid, or the like, may be introduced at the C- or N-terminus of the oligopeptide. Cysteine is particularly preferred to facilitate covalent coupling to other peptides, to form polymers by oxidation or to form internal bridges within the oligopeptide via disulfide bonds.

Additionally, the oligopeptide sequences may differ from the natural sequences by modification according to a variety of well known biochemical reactions. Amino acid residues contained within the compounds, but particularly at the carboxy- or aminoterminus, can be modified by amidation, acetylation or substituted with other chemical groups which can, for example, change the solubility of the compounds without affecting their activity. Amino-terminus acylation (e.g., acetylation), thioglycolic acid amidation, terminal-carboxy amidation (such as with ammonia or methylamine) may be performed to provide stability, increased hydrophobicity or for polymerization, for example. Alternatively, certain amino acid residues contained within the disclosed compounds, and particularly at the amino-terminus, can also be modified by deamination in order to provide resistance to degradation in the host by endogenous peptidase enzyme cleavage. Such deamination can be accomplished in the synthesized peptide, for example, by employing L or D amino acid oxidase. Deamination can also be accomplished by substituting the appropriate α-keto acid for the desired amino-terminal amino acid residue.

The oligopeptides of the present invention can be prepared in a wide variety of ways. The peptides, because of their relatively short size, may be synthesized in solution or on a solid support in accordance with conventional techniques. Solid-phase peptide synthesis, for example, is commenced from the carboxyterminal-end of the peptide using an α-amino protected amino acid. t-Butyloxycarbonyl (Boc) protective groups can be used for all amino groups even though other protective groups are suitable. See, for example, Stuart and Young, *Solid Phase Peptide Synthesis*. 2d Edition, Pierce Chemical Co. (1984); and Tam et al., *J. Am. Chem. Soc.* (1983) 105:6442, which are incorporated herein by reference. Various automatic synthesizers are commercially available and can be used in accordance with known protocols and in accordance with instructions provided by the manufacturer. Also, specialty peptides can be ordered from a variety of commercial sources such as Bio Search, Inc., San Rafael, Calif., or Peninsula Laboratories, Belmont, Calif.

It will be readily appreciated by those skilled in the art of peptide synthesis that the intermediates which are prepared in accordance with the present disclosure during the course of synthesizing the present oligopeptides are themselves novel and useful compounds and are within the scope of the invention.

Alternatively, hybrid DNA technology may be employed, where a synthetic gene is prepared utilizing single DNA strands coding for the desired oligopeptides, or substantially complementary strands thereof. Where the single strands overlap, they can be brought together in an annealing medium for hybridization. The hybridized strands may then be ligated to form the complete gene, and, by choice of appropriate termini, the gene may be inserted into expression vectors. See, for example, Maniatis et al., *Molecular Cloning. A Laboratory Manual*, Cold Spring Harbor Laboratory (1982), which is incorporated herein by reference. By way of example, recombinant DNA technology may be used to express the whole extracellular domain of the receptor and each of the five immunoglobulin-like domains. The domains can be expressed individually or in different combinations to compete with the receptor for PDGF binding and therefore block the action of PDGF on the receptor.

As desired, fragments from the naturally-occurring sequence may be employed for expression of the peptide fragments, and conservative base changes can be incorporated, such that the modified codons code for the same amino acid. Similarly, non-conservative changes can be incorporated where the resulting amino acid sequence is to be changed as discussed previously.

The coding sequence may be extended at either of the 5'- or 3'-terminus, or both termini, to extend the peptide, while retaining its blocking sites. The extension may provide for an arm for linking, e.g., to a label, such as an enzyme, for joining two or more peptides together in the same chain, for providing antigenic activity, convenient restriction sites for cloning, or the like.

The DNA sequences or fragments thereof are typically placed in expression vectors for ultimate transfection into a suitable host, including prokaryotic and eukaryotic hosts. See, Winnacker, *From Genes to Clones*, VCH Publishers, New York (1987), which is incorporated herein by reference. The host can be cultivated to enhance or otherwise amplify expression of the desired polypeptides, which then may be purified in accordance with standard techniques.

The prokaryotic hosts for expression may include bacteria, such as *E. coli, S. typhimurium, S. marcescens*, or *B. subtilis*. A preferred host is an *E. coli* strain that contains a temperature-sensitive bacteriophage lambda CI857 gene, such as described in Lautenberger et al., *Gene Anal. Tech.* (1984) 1:63. Eukaryotic hosts may include yeast, filamentous fungi, and mammalian cells. The peptide of interest may also be produced by inserting the DNA sequence coding therefor into the genome for vaccinia virus, which is then propagated in a suitable mammalian cell and the peptide fragment of interest appearing in the envelope or other internal vaccinia virus protein. See U.S. Pat. No. 4,722,848, which is incorporated herein by reference.

It is not known whether the subject polypeptides occur naturally. The present invention, thus, is related particularly to the non-naturally-occurring forms of PDGF receptor fragments, such as in isolated or purified, or substantially pure form. Typically, the peptides will be in a substantially different environment than in the naturally-occurring state, for example, in admixture with pharmaceutical carriers or the like. The synthetically or recombinantly-produced peptides and their salts are preferred forms.

Suitable salts of the peptides according to the present invention are pharmaceutically-acceptable non-toxic salts. The peptides can form acid addition salts, for example with inorganic acids, especially mineral acids. For peptides having at least one carboxy group and at least one basic group, for example an amino group, internal salts can be formed. Also, for peptides containing at least one free carboxy group, especially those having more carboxy groups than basic groups, metal ammonium salts, such as alkaline metal and alkaline-earth metal salts, can be produced. Alternatively, salts may be formed with organic acids such as, for example, acetic, oxalic, tartaric, mandelic, and the like, or, salts formed with the free carboxyl groups may be derived from such organic bases a isopropylamine, trimethylamine, 2-ethylamino ethanol, histidine, procaine and the like. Of course, for isolation and purification one may utilize pharmaceutically-unsuitable salts, but only the pharmaceutically-acceptable non-toxic salts should be employed for therapeutic use.

Pharmaceutical formulations of the oligopeptides described herein will comprise a therapeutically-effective dose of one or more of the oligopeptides in combination with a pharmaceutically-acceptable carrier. The oligopeptide may comprise from about five to fifty contiguous amino acids of the 499 N-terminal residues of the PDGF receptor in combination with a pharmaceutically-acceptable carrier. The carboxy-terminal amino acid of the oligopeptide composition may be free or amidated, and the amino-terminal amino acid may be free or acetylated. The pharmaceutical compositions may be used in methods for treating a patient suspected of having or susceptible to a disease related to proliferation and/or migration of smooth muscle cells, such as atherogenesis, which methods comprise administering to the patient a therapeutically- or prophylactically-effective dose of the oligopeptide(s) or a pharmaceutically-acceptable salt thereof. The oligopeptides may also be used in a method of inhibiting smooth muscle cell proliferation, wherein the oligopeptide inhibits the binding of PDGF to the PDGF receptor or smooth muscle cells.

A "therapeutically-effective dose" of the oligopeptides of the present invention will be an amount sufficient to diminish smooth muscle cell proliferation below a level associated with pathological events, such as restenosis, and yet allow adequate wound repair. Of course, the amount of the therapeutically- or prophylactically-effective compound which is actually administered will depend on the condition of the subject being treated, the nature and severity of the disease, the body weight, and also on the mode of administration, as well as the judgment of the attending physician. If desired, the oligopeptides may be co-administered with other agents, such as heparin, aspirin, dipyridamole, tissue plasminogen activator, streptokinase, urokinase, sulfinpyrazone, suloctidil, the peptide Arg-Gly-Asp-Ser, and/or antibodies reactive with the PDGF receptor.

By way of example and not limitation, the inhibition of smooth muscle cell migration and proliferation by interfering with the binding of PDGF to the PDGF receptor may find use in a wide variety of therapeutic settings, such as the following:

treatment of coronary restenosis or renal or peripheral artery restenosis after angioplasty, atherectomy, or other invasive methods of plaque removal;

treatment of vascular proliferative phenomena and fibrosis associated with other forms of acute injury, such as pulmonary fibrosis associated with adult respiratory distress syndrome, renal fibrosis associated with nephritis, coronary stenosis associated with Kawasaki's disease, and vascular narrowings associated with other arteritides, such as Takayasu's arteritis;

prevention of narrowings in vein grafts;

prevention of narrowings due to accelerated vascular smooth muscle proliferation in transplanted organs (heart, kidney, and liver); and treatment or prevention of other fibrotic processes, such as scleroderma, myofibrosis, etc.

Additionally, as PDGF-induced activation is involved in the proliferation of certain tumor cells, notably certain glial-derived tumors and osteosarcomas, the peptides described herein may also be useful in treating certain tumors.

The peptide dosage can range broadly depending upon the desired effects and the therapeutic setting. Typically, dosages will be between about 0.01 and 10 mg/kg, preferably between about 0.05 to 0.5 mg/kg, body weight. Administration is preferably parenteral, such as intravenous on a daily basis for up to a week or as much as one to two months or more, all of which will vary with the peptide's size. If the peptides are sufficiently small (e.g., less than about 8-10 amino acid residues) other routes of administration can be utilized, such as intranasally, sublingually, or the like.

The pharmaceutical preparations according to the invention contain the customary inorganic or organic, solid or liquid pharmaceutically-acceptable carriers, optionally together with other therapeutically- or prophylactically-effective compounds and/or adjuncts, as mentioned above. Preferably used are solutions or suspensions of the active ingredient oligopeptides, especially isotonic aqueous solutions or suspensions, or also lyophilized preparations which are dissolved shortly before use. The pharmaceutical preparations may be sterilized and/or contain preservatives, stabilizers, wetting agents, emulsifiers, solubilizers, viscosity-increasing substances, salts for regulating the osmotic pressure and/or buffers, and also other proteins, for example, human serum albumin or human blood plasma preparations.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride or the like. In addition, if desired, the injectable pharmaceutical compositions may contain minor amounts of non-toxic auxiliary substances, such as wetting agents, pH buffering agents, and the like.

If desired, absorption-enhancing preparations (e.g., liposomes) may be utilized in the pharmaceutical preparations. Liposomes in aqueous dispersion containing a therapeutically-effective amount of an oligopeptide may be preferred in some instances. In particular, suitable liposomes are relatively homogeneous in size with a diameter of approximately $2 \times 10^{-8}$ to about $5 \times 10^{-6}$ m, consisting of one or more double layers of lipid components, for example amphipathic lipids, e.g., phospholipids, such as lecithin or phosphatidic acid, and optionally neutral lipids, for example cholesterol, enclosing an aqueous interior containing an oligopeptide of the invention.

In addition to the compounds of the present invention which display the desired activities described above, compounds of the invention can also be used as intermediates in the synthesis of additional compositions. Alternatively, by appropriate selection, compounds of the present invention whose activity levels are reduced or eliminated entirely can serve to modulate the activity of other compounds which inhibit the activity of PDGF, by, for example, binding to alternate receptors, stimulating receptor turnover, etc.

Suitable in vitro assays for determining the peptides' blocking capability can be performed using standard methods, one example of which follows (Escobedo, et al., *J. Biol. Chem.* (1988) 263:1482, which is incorporated herein by reference). Mouse fibroblasts (Balb 3T3) cells are grown to confluency (3-5 days) in DME-H21 media supplemented with 10% calf serum, rinsed twice with PBS and detached from the flasks with 2 mM EDTA (15 min, 37° C.). The cells are pelleted (300 xg, 3 min, 23° C.), resuspended in cold PBS to give $3 \times 10^5$ cells/assay point (approx. $2 \times 10^6$ cells/ml) and kept on ice. Assays are performed in triplicate in $12 \times 75$ mm polypropylene tubes to which are added: 50 $\mu$l platelet-poor plasma, PBS (50–300 $\mu$l ), 10–250 $\mu$l of 2 mM test peptide, 3T3 cell suspension (100–200 $\mu$l) and, after these were incubated for 30 to 60 min at room temperature, 10–20 $\mu$l of $^{125}$I-PDGF (35,000 CPM) to give a final volume of 500 $\mu$l. The tubes are covered and incubated for 45 min at 37° C. with vigorous shaking. Peptides are initially dissolved in dry-N$_2$ purged water to which 1/9 volume of 10X PBS is added. Radiolabeled PDGF is suspended in PBS containing 5 mg/ml BSA and is adjusted to pH 7 with NaOH or 1M HEPES. Assays are also performed in the presence of excess unlabeled PDGF to determine nonspecific binding to the cells. The reaction is terminated by placing the tubes in ice. The binding mixture is then carefully layered onto 700 $\mu$l of ice-cold 28.5% Ficoll-paque (Pharmacia) in PBS in 1.5 ml Eppendorf tubes, which are spun at 13,500 rpm for 10 min at 4° C. The supernate is carefully aspirated, the tips of the tubes cut off and the cell-associated $^{125}$I-PDGF quantitated in a gamma-counter (e.g., Beckman model 5500).

When the peptides of the present invention are polymerized to each other or conjugated to carriers, they are particularly useful for raising antibodies (polyclonal or monoclonal) against the PDGF. Where different peptides are used in the antigenic mixture, it is possible to induce the production of antibodies immunoreactive with several epitopes of the glycoprotein.

The subject oligopeptides may be employed linked to a soluble macromolecule, typically not less than about 5 kD, carrier. Conveniently, the carrier may be a poly (amino acid), either naturally-occurring or synthetic, to which antibodies are likely to be encountered in human serum. Examples of such carriers are poly-L-lysine, hemocyanin, thyroglobulin, albumins, such as bovine serum albumin, tetanus toxoid, etc. As desired, one or more different oligopeptides of the present invention may be linked to the same macromolecule.

The manner of linking the oligopeptide with the carrier is conventional, such reagents as p-maleimidobenzoic acid, p-methyldithiobenzoic acid, maleic acid anhydride, succinic acid anhydride, glutaraldehyde, etc. The linkage may occur at the N-terminus, C-terminus or at a site intermediate to the ends of the molecule. The peptide may be derivatized by linking, may be linked while bound to a solid support, or the like, to form antigens or for other uses.

Numerous methodologies are presently known in the art for producing monoclonal antibodies to the peptides. See, e.g., Goding, *Monoclonal Antibodies; Principles and Practice*, Academic Press, 2d Ed. (1986), which is incorporated herein by reference. Less preferred forms of immunoglobulins may be produced by methods well known to those skilled in the art, e.g., chromatographic purification of polyclonal sera to produce substantially monospecific antibody populations.

A commonly employed process for producing monoclonal antibodies involves fusion, under appropriate conditions, of an immortalizing cell line with a B-lymphocyte which produces the desired antibody. Immortalizing cell lines are well known in the art, and include lines which are of mammalian origin, typically of murine, rat, bovine, or human origins. They are generally tumor lines or cells obtained by transforming a normal cell line with, for example, Epstein-Barr virus. Any immortalizing line can be used to prepare the hybridoma of the invention.

Similarly, techniques for obtaining the appropriate lymphocytes from mammals injected with the target antigen are well understood. Generally, either peripheral blood lymphocytes and cells of human origin are desired, or spleen cells, if mammalian non-human sources are employed. A subject mammal is injected with repeated dosages of the purified antigen, and the mammal is permitted to generate the desired antibody producing spleen cells or blood lymphocytes before these are harvested for fusion with the immortalizing line.

Techniques for fusion are also well known in the art and, in general, involve mixing the cells with a fusing agent such as, most commonly, polyethylene glycol. Preparation of a hybridoma by fusing these two types of cells is, by now, well known in the art. Successful hybridoma formation is assessed and selected by standard procedures, such as, for example, HAT selection. From among successful hybridomas, those secreting the desired antibody are selected by assaying the culture medium for their presence. Ordinarily, this is done using immunoreaction-based assays, including, without limitation, Western Blot, Elisa, or RIA assays. The antibodies can be recovered from the medium using standard protein purification techniques.

Antibodies reactive with the oligopeptides of the present invention will find various diagnostic uses, e.g., in quantitating the concentration of PDGF receptor on smooth muscle cells in accordance with techniques well-known to those skilled in the art, such as, for instance, the "sandwich" assays described in U.S. Pat. No. 4,376,110, which is incorporated herein by reference. Also, the antibodies, particularly monoclonal antibodies, may serve as immunogens themselves for the production of anti-idiotype antibodies, where the idiotopes of the anti-idiotype antibodies may effectively mimic the epitope encoded by an oligopeptide described herein, or the anti-idiotype antibody may itself regulate the immune response to the receptor peptides.

The blocking oligopeptides of the present invention may also find several in vitro applications. For instance, if desired, the peptides may be used in a method for detecting antibodies in an individual to the PDGF receptor. Immunoassays, such as radioimmunoassays, enzyme-linked immunoadsorbent assays, etc., are well known to the skilled artisan. Typically a biological sample, such as serum, obtained from an individual suspected of containing antibodies to the PDGF receptor is contacted or otherwise combined with a composition comprising at least one oligopeptide of the invention and an immunocomplex (antigen-antibody complex) is allowed to form and detected. The oligopeptide may conveniently be immobilized on a solid phase immunoadsorbent, such as a microtiter well, polystyrene bead, particles, paper, and the like. The presence of PDGF receptor antibodies may then be detected with a labeled antibody which is specific for the oligopeptide, or with a detectably-labeled anti-antibody to the PDGF receptor antibodies. Suitable labels may be selected from the group consisting of radioactive isotopes (e.g., $^3$H, $^{125}$I, $^{131}$I, $^{32}$P, $^{35}$S, $^{59}$Fe , fluorescent labels (e.g., fluorescein isothiocyanate, rhodamine, phycoerythrin), chemiluminescent labels (e.g., luminol, imidazoles), bioluminescent labels (e.g., luciferase, luciferin) and enzymes (e.g., alkaline phosphatase, peroxidase, betagalactosidase). Of course, in the assays it is generally desirable to provide incubation conditions sufficient to maximize antibody-peptide interaction, since this will maximize the binding of labeled antibody and thereby increase the signal. The specific concentrations of labeled antibodies and oligopeptides, the time and temperature of incubation, as well as other assay conditions, can be varied depending on various factors including the concentration of antibody in the sample, the nature of the sample, and the like. Those skilled in the art will be able to optimize the assay conditions for each determination. Kits containing containers for the materials for use in the assays may also be provided.

Other in vitro uses of the oligopeptides described herein include, for example, the affinity purification of PDGF from human platelets. Additionally, cells transfected with and expressing DNA sequences which encode an oligopeptide, where said transfected cells typically do not express the native receptor protein, may be used to determine the effect of PDGF drug analogues or inhibitors on cellular mitosis and/or migration. In another embodiment the oligopeptides themselves may be used and need not be expressed on a cell to test a drug's ability to function as a PDGF analogue or antagonist. The oligopeptide and compound to be analyzed may be tested in an assay format similar to that described hereinabove for determining the peptide's blocking capability.

Although the present invention has been described in some detail by way of illustration for purposes of clarity of understanding, it will be apparent that certain changes and modifications may be practiced within the scope of the amended claims.

What is claimed is:

1. A blocking oligopeptide comprising at least about five contiguous amino acids from an oligopeptide of the formula:

X—Val—Leu—Thr—Cys—Ser—Gly—Ser—Ala—Pro—Val—Val—Trp—Glu—Arg—Met—Ser—Z;  I

X—Gly—Glu—Tyr—Phe—Cys—Thr—His—Asn—Asp—Ser—Arg—Gly—Leu—Glu—Thr—Asp—Glu—Arg—Lys—Arg—Leu—Z;  II

X—Thr—Ile—Pro—Cys—Arg—Val—Thr—Asp—Pro—Gln—Leu—Val—Val—Thr—Leu—His—Z;  III

X—Arg—Ser—Tyr—Ile—Cys—Lys—Thr—Thr—Ile—Gly—Asp—Arg—Glu—Val—Asp—Ser—Asp—Ala—Tyr—Tyr—Val—Z;  IV

X—Thr—Leu—Met—Cys—Ile—Val—Ile—Gly—Asn—Glu—Val—Val—Asn—Phe—Glu—Trp—Z;  V

X—Thr—Tyr—Thr—Cys—Asn—Val—Thr—Glu—Ser—Val—Asn—Asp—His—Gln—Asp—Glu—Lys—Ala—Ile—Asn—Z;  VI

X—Thr—Leu—Gln—Val—Val—Phe—Glu—Ala—Tyr—Pro—Pro—Pro—Thr—Val—Leu—Trp—Z;  VII

X—His—Tyr—Thr—Met—Arg—Ala—Phe—His—Glu—Asp—Ala—Glu—Val—Gln—Leu—Ser—Phe—Gln—Leu—Gln—Z;  VIII

X—Thr—Val—Arg—Cys—Arg—Gly—Arg—Gly—Met—Pro—Gln—Pro—Asn—Ile—Ile—Trp—Z;  IX

X—Ser—Val—Arg—Cys—Thr—Leu—Arg—Asn—Ala—Val—Gly—Gln—Asp—Thr—Gln—Glu—Val—Ile—Val—Val—Z;  X

X—Gln—Asp—Gly—Thr—Phe—Ser—Ser—Val—Leu—Thr—Leu—Thr—Z;  XI

X—Leu—Gln—Val—Ser—Ser—Ile—Asn—Val—Ser—Val—Asn—Ala—Val—Gln—Thr—Val—Val—Arg—Gln—Gly—Z;  XII

X—Ser—Ile—Leu—His—Ile—Pro—Ser—Ala—Glu—Leu—Z;  XIII

X—Glu—Thr—Arg—Tyr—Val—Ser—Glu—Ile—Thr—Leu—Val—Arg—Val—Lys—Val—Z;  XIV or

X—Ile—Asn—Val—Pro—Val—Arg—Val—Leu—Glu—Leu—Ser—Glu—Ser—His—Pro—Z  XV wherein:
X, if present, is hydrogen, amido, acetyl, or additionally includes an amino acid, dipeptide, tripeptide or a polypeptide of up to 50 amino acid residues;
Z, if present, is hydroxyl, amido, or additionally includes an amino acid, dipeptide, tripeptide or a polypeptide of up to 50 amino acid residues;
the amino contiguous acids are not selected from X or Z, and
the blocking oligopeptide has less than about 50 natively associated amino acids, wherein the blocking oligopeptide is capable of specifically binding to platelet derived growth factor and/or its receptor.

2. A blocking oligopeptide according to claim 1, wherein the blocking oligopeptide is a salt.

3. A blocking oligopeptide according to claim 1, wherein the carboxy-terminal amino acid is free or amidated.

4. A blocking oligopeptide according to claim 1, wherein the amino-terminal amino acid is free or acetylated.

5. A pharmaceutical formulation comprising a blocking oligopeptide according to claims 1, 2, 3, or 4 in combination with a pharmaceutically-acceptable carrier, wherein the blocking oligopeptide is present in an amount sufficient to inhibit smooth muscle cell migration and proliferation by interfering with the binding of platelet-derived growth factor to the platelet-derived growth factor receptor.

* * * * *